United States Patent [19]
Greenfield

[11] Patent Number: 5,261,871
[45] Date of Patent: Nov. 16, 1993

[54] ORTHOPEDIC DEVICE

[76] Inventor: Raphael L. Greenfield, 4122 NW. 28th Way, Boca Raton, Fla. 33434

[21] Appl. No.: 806,629

[22] Filed: Dec. 12, 1991

[51] Int. Cl.$^5$ .............................................. A61F 5/00
[52] U.S. Cl. ....................... 602/26; 602/62; 602/19
[58] Field of Search ................. 602/26, 62, 19, 63; 128/80 C; 2/24, 22, 44; 482/105; 273/189 A, 189 R; 420/451, 446; 433/19, 20, 21; 148/402

[56] References Cited

U.S. PATENT DOCUMENTS

| | | | |
|---|---|---|---|
| 3,084,685 | 4/1963 | Lewis | 602/26 |
| 3,278,184 | 10/1966 | Rosenbaum | 482/105 |
| 3,804,084 | 4/1974 | Lehman | 602/26 |
| 3,883,885 | 5/1975 | Orlando | 148/402 X |
| 3,924,851 | 12/1975 | Winston | 482/105 |
| 3,990,709 | 11/1976 | DeRogatis | 273/189 A |
| 4,064,874 | 12/1977 | Valin | 128/80 |
| 4,116,236 | 9/1978 | Albert | 602/26 |
| 4,130,115 | 12/1978 | Taylor | 128/80 |
| 4,244,140 | 1/1981 | Kim | 148/402 X |
| 4,366,813 | 1/1983 | Nelson | 128/80 |
| 4,425,912 | 1/1984 | Harper | 128/80 |
| 4,445,505 | 5/1984 | Labour et al. | 128/80 |
| 4,790,624 | 12/1988 | Van Hove et al. | 128/46 M X |
| 4,909,510 | 3/1990 | Sahatjian | 273/73 R |
| 4,943,326 | 7/1990 | Ozawa et al. | 148/402 X |
| 4,986,263 | 1/1991 | Dickerson et al. | 128/80 |
| 5,038,760 | 8/1991 | Osborn | 602/19 |
| 5,046,948 | 9/1991 | Miura | 433/20 X |
| 5,103,807 | 4/1992 | Makaran | 602/21 X |

FOREIGN PATENT DOCUMENTS

| | | | |
|---|---|---|---|
| 101132 | 9/1961 | Denmark | 128/80 C |
| 48403 | 3/1984 | France | 128/80 C |

OTHER PUBLICATIONS

Wayman, C. M., "Some Applications of Shape-Memory Alloys," Journal of Metals, Jun. 1980, pp. 129-137.

Primary Examiner—Richard J. Apley
Assistant Examiner—Beverly A. Meindl
Attorney, Agent, or Firm—Lloyd L. Zickert

[57] ABSTRACT

An improved elastic orthopedic support brace having a plurality of pockets capable of receiving flexible wire members of varying sizes and configurations for providing adjustable lateral support for a joint and adjustable resistance against the flexion of that joint so that the brace may be customized for a patient having a particular injury.

16 Claims, 4 Drawing Sheets

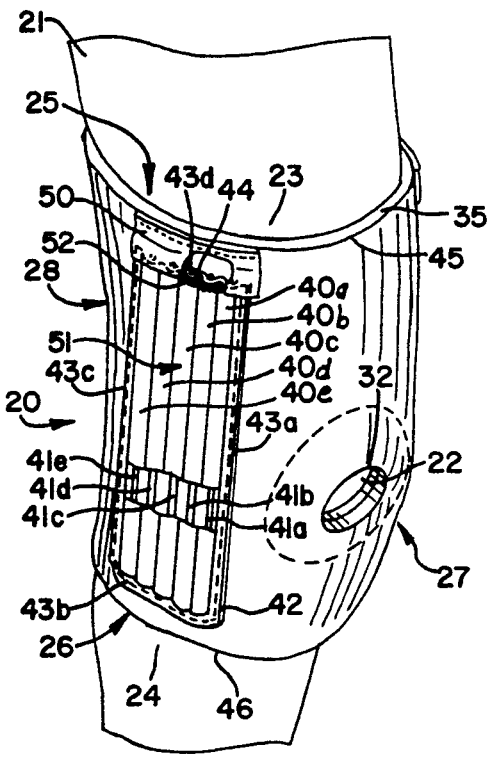
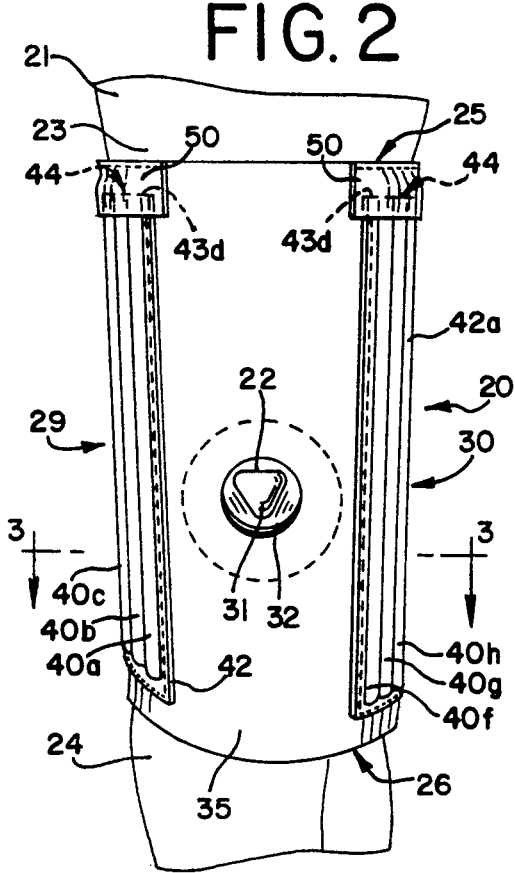
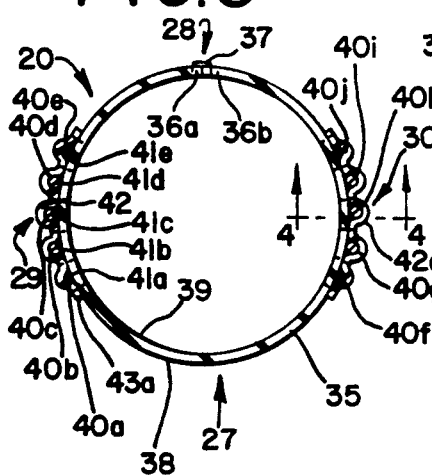
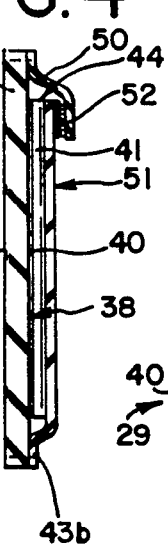
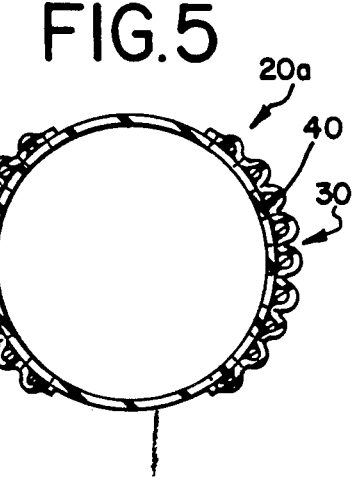

FIG. 6
FIG. 7
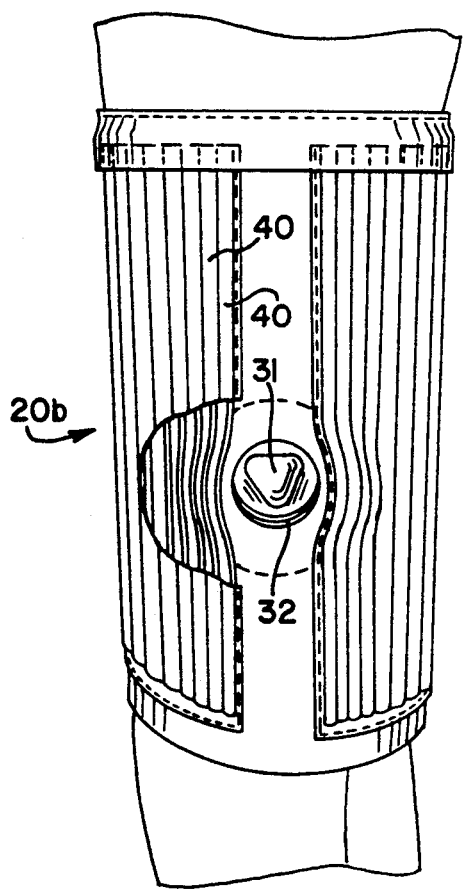
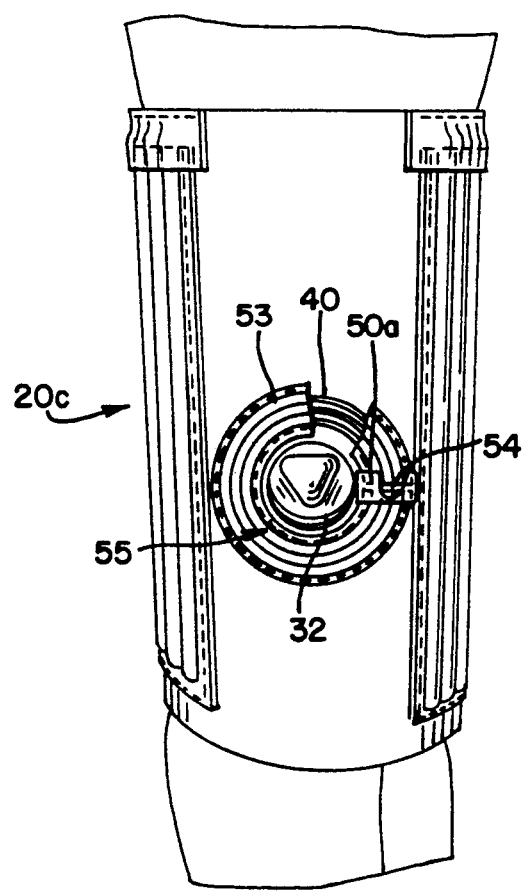

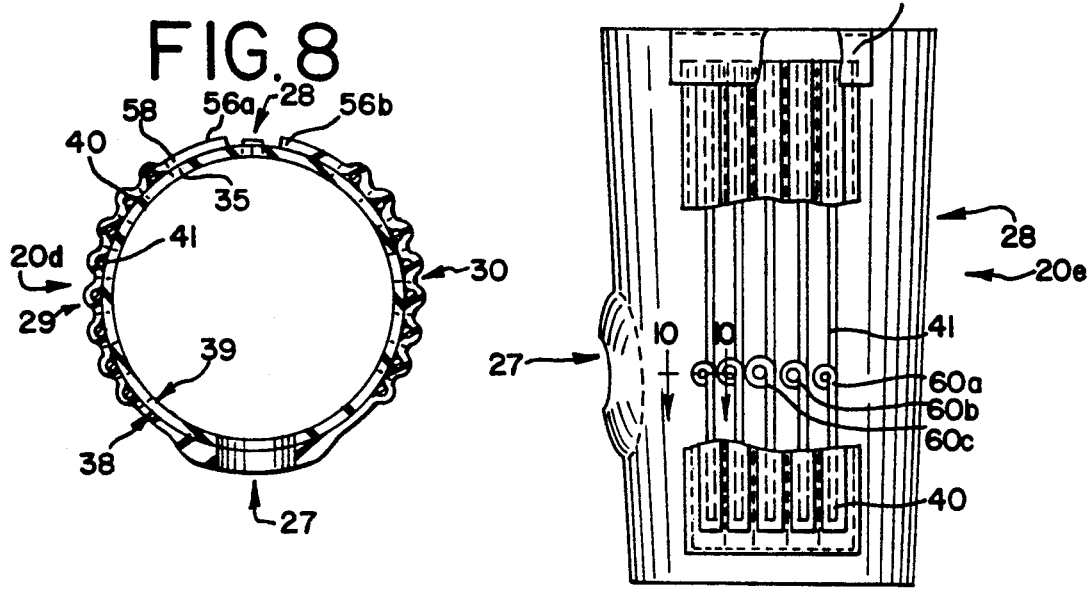
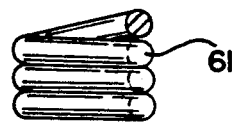
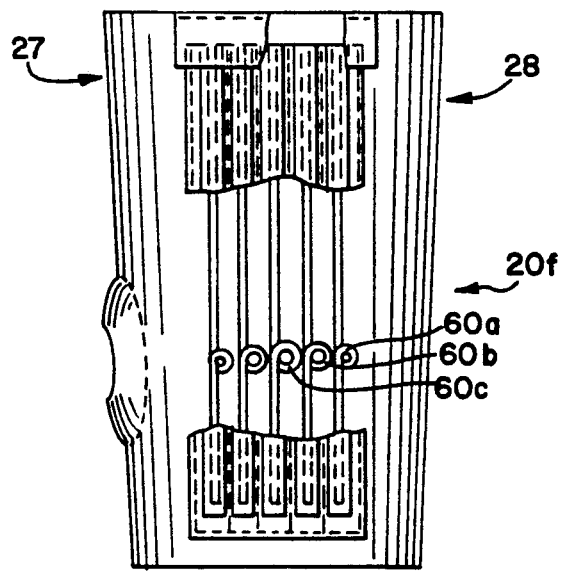

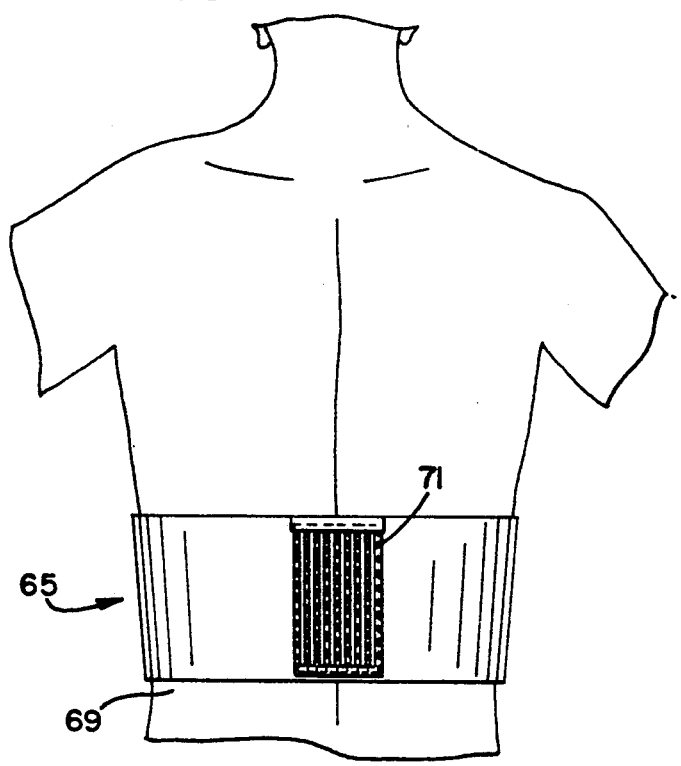
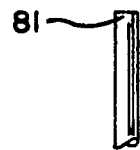
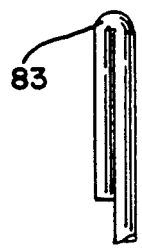
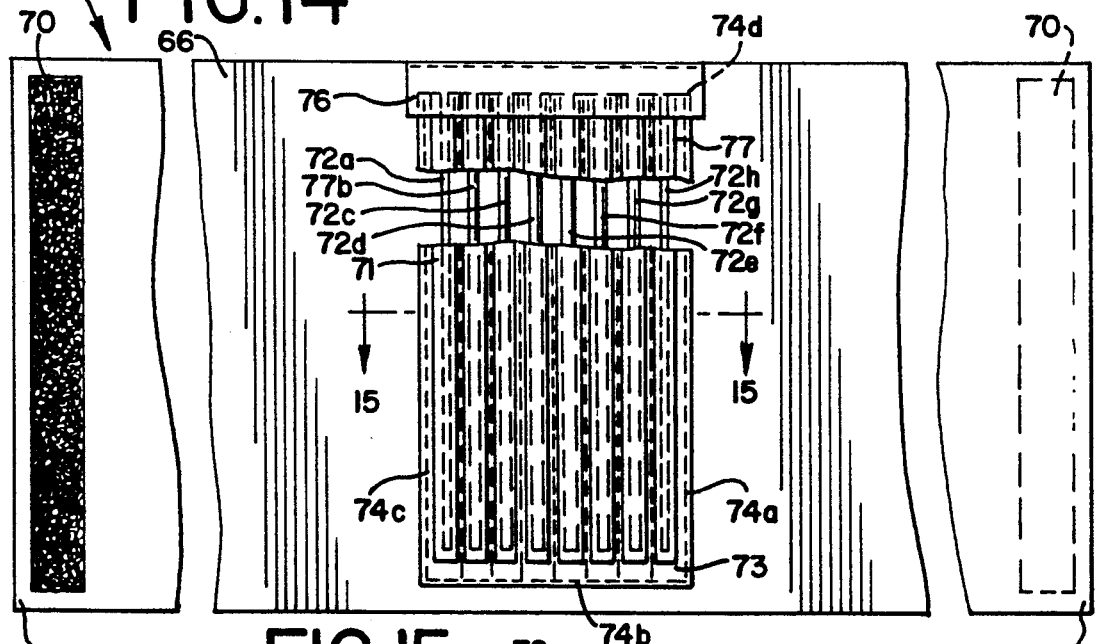

ORTHOPEDIC DEVICE

DESCRIPTION

This invention relates in general to an improved orthopedic device and more particularly to an elastic orthopedic support brace having a plurality of pockets suited to receive varying size wire members of nickel titanium wire, thereby providing adjustable support and adjustable resistance.

BACKGROUND OF THE INVENTION

Heretofore, it has been well known to provide orthopedic support devices for the joints of the body. Such orthopedic support devices are commonly used for the major articulated joints of the body including the knee, the ankle, the elbow, the wrist, the neck, the hip, the shoulder, and the back or spine. These orthopedic devices are used to protect injured joints, joints undergoing rehabilitation, previously injured joints, arthritic joints, and any other type of weakened joints.

While daily activities may not place excessive stress on these weakened joints, some activities such as athletic participation and competition can place a tremendous amount of stress on these joints. Although healthy joints may tolerate such stress without any additional support, orthopedic support is usually recommended for weakened joints.

Generally, an orthopedic support protects a joint from lateral motion in a direction transverse to the plane of flexion and extension of the joint while the joint is in a resting position or in motion. An orthopedic support may also protect the joint from significant rotational movement. At the same time, the orthopedic support should not interfere with normal flexion and extension of the joint. While not interfering with this movement, the support should be able to provide resistance to the flexure of the joint to assist in the ongoing rehabilitation of the joint and continual strengthening of that joint, together with the muscles, tendons and ligaments.

Various devices have been previously developed to provide orthopedic support to the joints during daily activity as well as during athletic activity. These devices are typically represented by those disclosed in U.S. Pat. Nos. 4,064,874; 4,130,115; 4,366,813; 4,425,912; 4,445,505; and 4,986,263.

Deficiencies of prior known devices include the inability to easily adjust the amount of lateral support, the inability to easily adjust the amount of resistance against flexure of the joint or for a certain area about a joint, the inability to increase or decrease support and resistance for different activities or different phases of treatment, the inability to provide support and resistance as determined by the individual's bone structure, and the lack of a device that provides support and resistance through light, continuous forces.

A wide variety in the amount, type, and location of support is necessary because each injury to a joint, each type of treatment for that injury, each rehabilitation process for that joint, and each physical activity which that joint can undergo will greatly differ for each person. Similarly, the proper amount, type, and location of resistance in flexure of the joint will vary depending on the original amount of damage to the joint, the location of that damage, the stage of rehabilitation, the overall strength of the joint, and the activity which the joint will undergo. Thus, while many heretofore known devices provide support for an injured joint, it has not been known to provide an orthopedic device in which the amount of support and the amount of resistance can be easily adjusted, depending on requirements for a particular patient, or that can be changed during treatment to accommodate changing conditions.

Heretofore known devices have not used light, continuous forces to provide the support and resistance in orthopedic devices even though light, continuous forces have proved effective in treating other deformities such as in orthodontically treating malpositioned teeth. More particularly, the use of nickel titanium wire has become widespread in orthodontics because of its excellent memory properties and capability of providing light, continuous forces.

SUMMARY OF THE INVENTION

The present invention overcomes the problems heretofore known by providing an orthopedic support or brace for a malfunctioning articulated joint of the human body in which the amount, type, and location of lateral support can be easily adjusted for each individual patient at the beginning and during treatment of that person by a prescribing professional. The present invention also overcomes the problems heretofore known by providing an orthopedic support in which the amount, type, and location of resistance against flexure of the joint is easily adjusted for each individual patient at the beginning and during treatment of that person by a prescribing professional. Moreover, the present invention uses nickel titanium wire, which produces light, continuous forces to create this support and resistance.

The orthopedic brace of the present invention is made from a tubular piece of elastomeric material sized to suitably cover a joint and its surrounding area. The brace includes a plurality of pockets for receiving a plurality of wire members providing support or reinforcement of the brace. When the wire members are inserted into the pockets, the wire members add stiffness to the elastomeric material while permitting a certain amount of flexibility. When several of the wire members are placed in adjacent pockets, the combination of the wire members in these adjacent pockets provide sufficient lateral support to protect a joint. These wire members also provide resistance against the flexure of the joint. Furthermore, the number of pockets, the number of wire members, the interchangeability of the wire members, the shapes of the wire members, and the size of these wire members can vary, thus providing adjustable support and adjustable resistance. The orthopedic brace can be further customized to meet the needs of each individual patient by taking an X-ray or other image of the joint in at least two views, thereby providing the treating professional with the proper information to conform each wire member exactly to the individual's bone structure or architecture. Accordingly, treatment of a malfunctioning joint can be carefully prescribed to produce the best possible results at the beginning and at any time during treatment for each patient.

It is therefore an object of the present invention to provide a new and improved orthopedic support device for protecting and/or rehabilitating an articulated joint that provides easily adjustable support.

Another object of the present invention is to provide an orthopedic support device that provides easily adjustable resistance.

Still another object of the present invention is to provide an orthopedic support or brace which can be worn during daily activities and during athletic participation.

Another object of the present invention is to provide an orthopedic support having means that provides light, continuous forces.

Another object of the invention is to provide a tubular orthopedic brace of elastomeric material having a plurality of axially extending pockets for receiving resilient wire members for stiffening the brace at prescribed areas, wherein the wire members are of varying sizes to vary the stiffness in given areas, and wherein access is provided for the pockets for interchanging wire members to change the stiffness and area of stiffness.

Still another object of the invention is in the provision of a tubular orthopedic brace of elastomeric material having a plurality of pockets for interchangeably receiving wire members of varying sizes so that the stiffening of the brace may be changed over the treatment of a patient.

Yet another object of the present invention is to provide an orthopedic support which conforms to each individual bone structure and injury.

A further object of the invention is in the provision of an orthopedic brace for an articulated joint having stiffening means that can vary the stiffness and flexure along the brace to more particularly define variable stiffness and flexure to better treat a variety of malfunctioning conditions of a joint or of different persons.

Other objects, features and advantages of the invention will be apparent from the following detailed disclosure, taken in conjunction with the accompanying sheets of drawings, wherein like reference numerals refer to like parts.

DESCRIPTION OF THE DRAW

FIG. 1 is a side perspective view of one embodiment of the present invention, and more specifically an orthopedic knee brace with pockets for receiving wire members, shown worn on a person's leg and with parts broken away illustrating different size wire members;

FIG. 2 is a front perspective view of the orthopedic knee brace of FIG. 1;

FIG. 3 is a cross-sectional view of the orthopedic knee brace of FIG. 2 taken substantially along line 3—3 of FIG. 2;

FIG. 4 is a vertical sectional view through one of the pockets of the orthopedic knee brace taken substantially along line 4—4 of FIG. 3;

FIG. 5 is a cross-sectional view like FIG. 3 of another embodiment of an orthopedic knee brace illustrating a greater number of pockets on both sides of the knee brace;

FIG. 6 is a front perspective view of another embodiment of an orthopedic knee brace illustrating pockets adjacent to the patella opening;

FIG. 7 is a front perspective view of another embodiment of an orthopedic knee brace illustrating pockets surrounding the patella opening.

FIG. 8 is a cross-sectional view like FIG. 3 of still another embodiment of an orthopedic knee brace illustrating a different construction of the knee brace and a different number of pockets on both sides of the knee brace;

FIG. 9 is a side elevational view of another embodiment of an orthopedic knee brace of the invention differing from the embodiment of FIG. 1 in that the wire members include a loop at the flexure area facing the anterior of the knee;

FIG. 10 is a cross-sectional view of the loop in the looped wire member taken along line 10—10 of FIG. 9 and illustrating the construction of the a single loop in the wire member;

FIG. 11 is a cross-sectional view of another wire member embodiment of the invention illustrating a wire member with a plurality of loops;

FIG. 12 is a side elevational view like FIG. 9 but differing in that the loops of the wire members face the posterior of the knee;

FIG. 13 is an elevational view of another embodiment of the present invention, showing application of the orthopedic brace of the invention as an orthopedic back brace being worn at about the waist of a person to provide support to the lower back;

FIG. 14 is a greatly enlarged, partly broken elevational view of the orthopedic back brace of FIG. 13;

FIG. 15 is a cross-sectional view of the orthopedic back brace of FIG. 12 taken substantially along line 15—15 of FIG. 14;

FIG. 16 is a fragmentary elevational view of a wire member having a plain end according to the present invention;

FIG. 17 is a fragmentary elevational view of a wire member having a balled end; and FIG. 18 is a fragmentary side elevational view of a wire member having a doubled-over end.

DESCRIPTION OF THE INVENTION

The present invention can be used in conjunction with any articulated joint of the body including the ankle, the knee, the elbow, the wrist, the neck, the hip, the shoulder, and the back or spine. For simplicity, the knee brace and the back brace are used as examples to illustrate the present invention.

The knee brace of the present invention has an elastomeric or stretchable tubular sleeve which snugly covers the joint and the surrounding area. The tubular sleeve has a plurality of adjacent vertically extending pockets disposed on opposing sides of the knee brace in alignment with the hinge axis of the joint. Each pocket is capable of receiving a wire member. Preferably, the wire members are of round nickel titanium alloy. The placement of several of these wire members in adjacent pockets or in close proximity stiffens that part of the elastomeric tubular body. This stiffening of an area of the sleeve allows the knee brace to laterally support the knee, permitting flexion and extension of the joint while inhibiting lateral movement. The wire members are interchangeable with wire members of different sizes to produce different stiffness levels, which also allows varying the stiffness along the area of the pockets. The wire members inserted into the pockets further provide resistance against flexure of the knee.

The back brace of the present invention has an elastomeric generally rectangular member which has a fastening means on its opposite ends to allow those ends to be connected so as to define a tubular brace. Similarly, the knee brace could be formed in this manner. The back brace is worn by placing it around the waist or lower back area of a person and then fastening the two opposite ends together. The back brace has a plurality of adjacent pockets suited to receive wire members for adding lateral support and resistance to the elastomeric material in the area where stiffness is desired for each individual patient.

Referring now to the drawings, one embodiment of the present invention, the knee brace 20, is disclosed in FIGS. 1, 2, 3, and 4. The tubular shaped knee brace 20 is worn around a person's leg 21. Specifically, the knee brace 20 closely covers and fits snugly around the knee 22, the lower portion of the thigh 23, and the upper portion of the calf 24. The knee brace 20 is slipped onto a leg 21, by inserting the leg through two openings, a top opening 25 and bottom opening 26, in the knee brace 20. The knee brace 20 is manufactured from elastomeric, stretchable, and/or flexible type materials.

While generally tubular, it is convenient to describe a knee brace 20 worn on a person's leg 21 as having four sides corresponding to the sides of the knee 22, specifically the anterior side 27, the posterior side 28, the outer side 29, and the inner side 30. The anterior side 27 abuts the patella or the kneecap 31; the posterior 28 abuts the back of the knee 22; the outer side 29 abuts the side of the knee facing away from the leg 21; and the inner side 30 abuts the side of the knee 22 facing the opposite leg 21.

The anterior side 27 is constructed with an appropriate hole 32 which should be positioned over the patella or the kneecap 31. Hole 32 provides room for the patella or the kneecap 31 and assists in the proper orientation or positioning of the knee brace 20 on the leg 21. It should be appreciated that the size and shape of this hole 32 may vary depending on the size of the knee brace 20 and ultimately upon the size of the knee 22.

The knee brace 20 primarily consists of a tubular shaped sleeve 35 formed from a generally rectangular piece of elastomeric material, of which two sleeve ends 36a and 36b are stitched together to form a seam 37. This sleeve 35 has an outer wall 38 which faces away from the leg 21 and an inner wall 39 which faces and physically touches the knee 22, the thigh 23, and the calf 24 when the knee brace 20 is worn on a person's leg 21. The sleeve 35 snugly covers the area around the knee 22, providing a certain amount of support for the knee 22. However, this support does not provide sufficient protection for the knee 22 from undesired lateral movement. It should be appreciated that the sleeve 35 need not be rectangular; in fact, it is well know to shape the sleeve 35 to generally fit the curvature of the knee 22, the thigh 23, and the calf 24.

The knee brace 20 has a plurality of adjacent vertically extending pockets 40 for receiving wire members 41. The knee brace 20 illustrated in FIGS. 1, 2, 3, and 4 has five pockets 40a, 40b, 40c, 40d and 40e on its outer side 29 and five pockets 40f, 40g, 40h, 40i, and 40j on its inner side 30. The series of pockets at the outer side, as well as the series of pockets at the inner side, align generally with the hinge axis of the joint and at each side of the axis so as to give lateral support to the joint. Each of the pockets includes a wire member 41 for stiffening the brace along the area of influence of the wire member. Respectively, wire members 41a to 41j are received in pockets 40a to 40j. The pockets 40 on the outer side 29 are formed by stitching a section of material 42 to the outer wall 38 at the outer side 29 of the sleeve 35. Specifically, three of the four edges 43, the right edge 43a, the bottom edge 43b, and left edge 43c of this section of material 42 are stitched on the outer wall 38 at the outer side 29. This section of material 42 is also stitched to the sleeve 35, at regular intervals between edges 43a and 43c leaving enough material between each interval to form each pocket 40. The top edge 43d is left unstitched and thereby forms the pocket openings 44 through which the wire members 41 are inserted into the pockets 40. During treatment of a patient, wire members of other sizes may be interchanged for those first used. The pockets 40 extend from near the upper edge 45 of the sleeve 35 to near the lower edge 46 of the sleeve 35. It should be appreciated that the height and size of the pockets 40 as well as the construction of the pockets 40 can vary greatly. It should also be appreciated that other methods, such as gluing, could be used to attach the section of material 42 to the sleeve 35.

A flap 50 for covering the pocket openings 44 is connected on the outer wall 38 of the outer side 29 of the knee brace 20 above the pocket openings 44. This flap 50 extends downwardly and overlies or drapes over the pocket openings 44 where it is fastened to the face 51 of the pockets 40 by a hook loop type Velcro fastener 52. The flap 50 covers and thereby closes the pocket openings 44 which prevents the wire members 41 from exiting the pocket openings 44. This flap 50 is easily unfastened to allow the removal of wire members 41 from the pockets as well as the insertion of wire members 41 into the pockets. It should be appreciated that other types of flaps could be used to secure the wire members in the pockets and that other fastening methods could be used to attach the flap 50 to the face 51 of the pockets 40.

The pockets 40f to 40j on the inner side 30 of the knee brace 20 are constructed with a similar section of material 42a in an identical fashion to the outer side 29 of the knee brace. The number of pockets 40 on the outer side 29 may be equal or unequal to the number of pockets 40 on the inner side 30. For certain types of injuries, greater support may be required on one side of the knee 22 than on the other and the exact location of support and resistance may vary.

When a wire member 41 is inserted into a pocket 40 and the flap 50 is closed, the wire member stiffens the area of the sleeve 35 surrounding that pocket 40. The wire member also adds resiliency to the area surrounding that pocket 40. When further wire members are inserted into the adjacent pockets, the entire area stiffens and the level of resiliency increases. This provides the knee brace 20 with lateral support and resistance.

The cross-sectional diameter of the wire members 41 inserted into the pockets 40 can vary as illustrated in FIGS. 1 and 3. For instance, a relatively thin wire member 41a having a given diameter can be inserted into a pocket 40a as shown in FIGS. 1 and 3. This wire member 41a provides a certain amount of support and resistance. A similar wire member having the same diameter could be inserted into each of the pockets 40b–40e, thereby increasing the support and resistance with each additional wire member. On the other hand, where greater lateral support is desired, a relatively thicker wire member 41b, as illustrated in FIGS. 1 and 3, having a larger diameter than wire member 41a could be inserted into pocket 40b, for instance, to provide greater lateral support for the knee 22 as well as increasing the amount of resistance upon the flexion of the knee 22. A combination of different size wires members can be used to vary this support and resistance. Of course, the size of the wire members can greatly vary, being limited only by the size of the pockets 40. An important feature of the present invention is that all of the pockets 40 are capable of receiving varying size wire members.

The placement of varying size wire members 41 can also be used to provide support and resistance for different locations in the knee 22. For instance, as shown in FIGS. 1 and 3, the smaller diameter wire member 41a is in pocket 40a closer to the anterior side 27 of the knee brace 20 and the larger diameter wire members 41b, 41c and 41d are in pockets 40b, 40c and 40d, respectively. A smaller diameter wire member 41e is in pocket 40e. The placement of these wire members can vary, thereby varying the exact amount of support and resistance and varying the location of the support and resistance as desired for each individual patient by the prescribing professional.

Similarly, an advantage of the present invention is the ability to change the size of the wire members, thereby increasing or decreasing support and resistance at the joint or knee. For example, when the knee brace 20 is first worn, relatively smaller diameter wire members may be inserted in alternating pockets as prescribed by the treating professional. As the knee strengthens, a smaller diameter wire member may be placed in the empty pockets, as determined necessary by the treating professional. As rehabilitation continues, the smaller wire member can be replaced with relatively larger wire members, again as determined necessary by the treating professional. Thereby, the lateral support and resistance can increase slowly as the knee gains strength and more stress is placed on the knee. Another important feature of the present invention is the composition of the cylindrical or round wire members which provide lateral support and resistance in the knee brace 20. The wire members are made from a nickel titanium alloy. Nickel titanium is a superelastic metal which has very good springback, resiliency, flexibility, and memory properties. It produces soft or light, continuous forces which have been determined to be extremely effective in treating ailments of the body. For instance, this type of wire is widely used as orthodontic archwire for braces because this wire slowly and with light, but continuous forces moves the teeth into correct positions. The same type of forces will be appropriate for rehabilitating and strengthening injured or weakened joints.

Another embodiment of the present invention is illustrated in cross section in FIG. 5. This figure illustrates a knee brace 20a with a greater number of pockets 40 on each side. This knee brace has nine pockets 40 on the outer side 29 and nine pockets 40 on the inner side 30. This embodiment demonstrates that the number of pockets 40 can significantly vary. Of course, if the knee brace 20a is the same size as the knee brace 20, the pockets 40 will extend farther around the sides of the knee brace 20 unless the pockets 40 are constructed with a smaller width. Depending on the number of pockets and their size, the size of the wire members 41 might be limited. Again, the placement of varying size wire members 41 can vary greatly, as illustrated in FIG. 5.

Another embodiment of the knee brace 20b is illustrated in FIG. 6. In this embodiment, the pockets 40 are constructed adjacent to the hole 32 for the kneecap 31. These pockets may be bent or curved to conform to the shape of the patella. Wire members 41 of varying sizes can be placed in these pockets to add support to the orthopedic brace around the area of the patella. The wire members inserted in the curved or bent pockets will take the shape of those pockets, thereby adding support for the area surrounding the patella.

Another embodiment of the knee brace 20c is illustrated in FIG. 7. In this embodiment, there are a series of circular pockets 53 which are constructed around the hole 32. A wire member 40 can be inserted through each circular pocket opening 54 and into each of these pockets 53, thereby providing additional support for the kneecap 31 and surrounding area. The circular pocket openings are covered and closed by a flap 50a, which is similar to flap 50, such that the flap can be releasably secured to the circular pocket face 55 by a hook-loop type Velcro fastener or any other appropriate fastening device.

Another embodiment of the knee brace 20d is illustrated in FIG. 8. In this embodiment, only one strip of material 58 is stitched to the sleeve 35 to form the pockets 40 on both the outer side 29 and the inner side 30. In this embodiment, one end 56a of the strip of material 58 is stitched on the outer wall 38 at the posterior side 28 of the knee brace 20. The strip of material 58 is then stitched to the outer side 29 of the knee brace 20 at regular intervals to form pockets 40 on that side. The strip of material 55 is then draped over the anterior side 27 of the knee brace 20 and stitched to the sleeve 35 on the inner side 30 to form pockets 40 on that side. Finally, the other end 56b of the strip of material 58 is stitched to the posterior side 28. This embodiment illustrates the construction of the pockets and the entire knee brace from two pieces of material. The number of pieces of material and the construction of the pockets can vary. The pockets 40 formed in this embodiment are similarly suited to receive the wire members 41. It should be noted that this embodiment has eight pockets 40 on each side. As previously explained, the number of pockets can vary and the number of pockets can be odd or even. It should also be appreciated that both the sleeve 35 and the strip of material 58 can have a hole for the kneecap.

Another embodiment of the knee brace 20e has a variation in the construction of the wire member 41 as illustrated in FIGS. 9 and 10. The wire member 41 in this embodiment is formed with a loop or coil 60. This loop or coil faces the anterior side 27 of the knee brace 20e. The loop or coil must have a smaller diameter than the width of the pocket 40 to fit into that pocket. The loop or coil 60 is bent or formed in the wire member 41 at an intermediate position between the ends of the wire member 41 such that it is at the level of the flexion in the knee or the joint when the wire member 41 is inserted into the pocket 40. This loop 60 in the wire member 55 decreases the resistance against flexion of the knee compared to a straight wire member 40 as well as increasing the amount of support against lateral movement. The size of the loop or coil can also vary, as illustrated in FIG. 9. Loop 60a, 60b and 60c can be of varying sizes, limited only by the size of the pockets. These varying size loops also allow a treating professional to adjust and vary the support and resistance. It should be appreciated that any type of helix could be used instead of a loop or coil. The construction of the sleeve 35, pockets 40, and the flap 50 is the same as in the prior embodiments.

The wire member can also be made with multiple loops or a stacked coil 61, as specifically illustrated in FIG. 11. This stacked coil 6 will provide additional support and resistance. The number of loops 60 in the wire member 41 will be limited by the size of the pocket 40.

The wire member 41 with a single loop 60 or a stacked coil 61 can also be inserted in the pocket 40 with the loop facing the posterior side 28 of the knee brace 20f as shown in FIG. 12. This will provide more resistance than a straight wire member and therefore more resistance than a wire member with the loop facing the anterior side 27 of the knee brace. The loops 60a, 60b and 60c may also be of varying sizes in this embodiment of the knee brace 20f, as illustrated in FIG. 12.

Another embodiment of the present invention is a back brace 65 as illustrated in FIGS. 13, 14, and 15. The back brace 65 has a sleeve 66 constructed from a substantially rectangular piece of elastomeric material. Unlike the knee brace 20, the opposite ends 67a and 67b of the sleeve 66 are not stitched together to enable a person 68 to put on the back brace 65 by wrapping it about his/her lower torso 69 as shown in FIG. 13. A releasable fastening method such as a hook loop Velcro type fastener 70 is used to fasten together the opposite ends 67a and 67b of the sleeve 66. Of course, other fastening means could be used to connect these ends.

The back brace 65 has a plurality of vertically extending pockets 71 for receiving varying size wire members 72. These pockets 71 are similarly constructed as the pockets 40 of the knee brace 20. The pockets 71 are formed by stitching a section of material 73 to the sleeve 66 in a similar manner as in the knee brace 20. Three of the four edges 74a, 74b, and 74c of the section of material 73 are stitched to the sleeve 66 leaving the top edge 74d of the section of material 73 open. The section of material 73 is also stitched to the sleeve 66 at regular intervals to form the pockets 71 as specifically illustrated in FIG. 15. It should be appreciated that the section of material 73 could be stitched to either wall of the sleeve, however it is preferable to stitch it to the outer wall 75.

Also similar to the knee brace 20, a flap 76 is used to cover the open pockets 71 and to secure the wire members 72 in the pockets 71. The flap 76 is connected to the sleeve 66 and is fastenably secured to the outside face 77 of the pockets 71.

The wire members 72 in the back brace 65 are similar to those used in the knee brace 20. The wire members 72 can be of a relatively small diameter such as 72a and 72h, or of a relatively larger diameter such as 72b and 72g, or yet even a relatively larger diameter, such as 72c, 72d, 72e and 72f. The wire members function in a similar manner to the wire members 41 of the knee brace 20 and have all of the features previously described. Likewise, the back brace 65 functions in a similar manner as the knee brace 20.

It should be appreciated that the wire members used in the present invention can have ends which vary in shape and form. For instance, FIG. 16 illustrates a wire member which has a plain end 81, there being no modification after the wire is cut. FIG. 17 illustrates a wire member that has a balled end 82. FIG. 18 illustrates a wire member which is bent over itself or doubled back and forms a doubled-over end 83. The balled end 82 and the doubled-over end 83 are preferable in this invention because they allow the wire member to be inserted into the pocket without snagging or piercing the material which form the pockets. Other configurations or methods to smooth the ends of the wire member could be used.

The above devices, particularly the knee brace and the back brace, have been illustrated and described as examples of the present invention. The present invention will also be suited to support other joints of the body such as the wrist, the elbow, the ankle, the hip, the shoulder, and the neck.

It will be understood that modifications and variations may be effected without departing from the scope of the novel concepts of the present invention, but it is understood that this application is to be limited only by the scope of the appended claims.

The invention is hereby claimed as follows:

1. An orthopedic device for protecting and/or rehabilitating a hinge axis joint of a person comprising: a sleeve constructed from elastomeric material for covering said joint, said sleeve having a plurality of elongated pockets at least at one side of the joint in general alignment with the hinge axis and having means permitting removal and interchange of the contents of said pockets; a plurality of round, flexible wire members in said pockets encompassing the characteristics of springback, resiliency, flexibility, and memory properties which produce soft, light continuous forces, at least some of said wire members having distinct stiffness values; whereby said wire members are adapted to be removed from said pockets and interchanged for wire members of other stiffness values thereby providing a predetermined amount of stiffening to said sleeve and varying amounts of lateral support and resistance along said joint to help strengthen said joint.

2. An orthopedic device as defined in claim 1, wherein said flexible wire members are a nickel titanium alloy.

3. An orthopedic device as defined in claim 1, wherein said plurality of pockets are located one each side of said joint, and said means for permitting the members to be removed and interchanged including having the pockets open at one end and cover means for selectively closing the open ends.

4. An orthopedic device as defined in claim 1, wherein said pockets are formed on said sleeve by attaching at least one piece of material to said sleeve.

5. An orthopedic device as defined in claim 1, wherein said wire members have at least one loop intermediate the ends thereof.

6. An orthopedic device as defined in claim 1, wherein said wire members are straight in their unflexed condition.

7. An orthopedic device as defined in claim 3, wherein said cover means includes a flap movable between open and closed positions relative to the open ends of the pockets.

8. An orthopedic device as defined in claim 7, which further includes means for releasably securing the flap in closed position.

9. An orthopedic device as defined in claim 1, wherein the device is for a knee joint and which further includes at least one circular pocket and wire member therein at least partially adding support for the area of the knee around the patella.

10. An orthopedic brace for an articulated joint comprising: a tubular body of elastomeric material, said body including an inside surface to engage the skin of a person and an outside surface, said body having a plurality of substantially parallel aligned pockets along the outside surface, said pockets being open at one end to permit removal ad interchange of the contents of said pockets; a plurality of round wire stiffening members encompassing the characteristics of springback, resiliency, flexibility and memory properties which produce soft, light continuous forces, at least some of said wire members having distinct stiffness values and being of various diameter; whereby said wire members are adapted to be removed from said pockets and interchanged for wire members of other stiffness values hereby providing a prescribable and adjustable amount of stiffening to said sleeve and varying amounts of stiffness and support along the joint.

11. An orthopedic brace as defined in claim 10, wherein the pockets are substantially parallel to each other to maintain the wire members in substantially parallel relation to each other.

12. An orthopedic brace as defined in claim 10, wherein said wire members are of graduated stiffens values from the centermost pocket to the outer most pockets.

13. An orthopedic brace as defined in claim 10, which further includes means for selectively covering the open ends of the pockets.

14. An orthopedic brace as defined in claim 13, wherein said covering means includes a flap connected along one edge to the body and sized to overlap the open ends of the pocket.

15. An orthopedic brace as defined in claim 14, wherein said flap includes means coating with means on the body to releasably secure the flap in closed position.

16. An orthopedic brace as defined in claim 10, wherein the wire members are a nickel titanium alloy.

* * * * *

UNITED STATES PATENT AND TRADEMARK OFFICE
CERTIFICATE OF CORRECTION

PATENT NO. : 5,261,871
DATED : November 16, 1993
INVENTOR(S) : Raphael L. Greenfield It is certified that error appears in the above-identified patent and that said Letters Patent is hereby corrected as shown below:

```
Col.  8, line 61, after "coil", change "6" to --61--;
Col. 10, line 61, change "ad" to --and--;
         line 67, change "diameter" to --diameters--;
Col. 11, line  2, change "hereby" to --thereby--;
         line 11, change "stiffens" to --stiffness--;
         line 12, change "outer most" to --outermost--; and
Col. 12, line  9, change "coating" to --coacting--.
```

Signed and Sealed this

First Day of March, 1994

Attest:

BRUCE LEHMAN

Attesting Officer

Commissioner of Patents and Trademarks